(12) United States Patent
Lee

(10) Patent No.: US 6,217,547 B1
(45) Date of Patent: Apr. 17, 2001

(54) LUBRICOUS AND READILY BONDABLE CATHETER SHAFT

(75) Inventor: Jeong Soo Lee, Diamond Bar, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/289,433

(22) Filed: Apr. 9, 1999

Related U.S. Application Data

(63) Continuation-in-part of application No. 08/976,447, filed on Nov. 25, 1997, which is a continuation of application No. 08/587,330, filed on Jan. 16, 1996, now abandoned.

(51) Int. Cl.[7] ............................................... A61M 29/00
(52) U.S. Cl. ........................................ 604/96.01; 604/103
(58) Field of Search ..................... 604/96.01, 523, 604/265, 93.01, 264, 103, 172, 103.11; 606/194

(56) References Cited

U.S. PATENT DOCUMENTS

| | | | |
|---|---|---|---|
| 3,458,596 | | 7/1969 | Faigle et al. .................... 260/857 |
| 4,616,064 | * | 10/1986 | Zukosky et al. .................. 525/92 |
| 4,814,231 | * | 3/1989 | Onohara et al. ............... 428/425.5 |
| 4,898,591 | | 2/1990 | Jang et al. ..................... 604/282 |
| 4,945,126 | | 7/1990 | Crosby et al. .................. 524/507 |
| 4,955,895 | * | 9/1990 | Sugiyama et al. ............... 606/194 |
| 5,041,100 | | 8/1991 | Rowland et al. ................ 604/265 |
| 5,267,959 | * | 12/1993 | Forman .......................... 604/103 |
| 5,304,134 | * | 4/1994 | Kraus et al. ..................... 604/96 |
| 5,344,400 | * | 9/1994 | Kaneko et al. ................... 604/96 |
| 5,348,538 | * | 9/1994 | Wang et al. ...................... 604/96 |
| 5,443,907 | * | 8/1995 | Slaikeu et al. .................. 428/375 |
| 5,501,759 | * | 3/1996 | Forman ......................... 156/272.8 |
| 5,503,631 | * | 4/1996 | Onishi et al. ..................... 604/96 |
| 5,533,968 | * | 7/1996 | Muni et al. ...................... 604/96 |
| 5,549,552 | * | 8/1996 | Peters et al. ..................... 604/96 |
| 5,554,120 | * | 9/1996 | Chen et al. ...................... 604/96 |
| 5,556,383 | * | 9/1996 | Wang et al. ...................... 604/96 |
| 5,769,819 | * | 6/1998 | Schwab et al. .................. 604/103 |
| 5,849,846 | * | 2/1999 | Chen et al. ..................... 525/166 |
| 5,868,706 | * | 2/1999 | Cox .............................. 604/96 |
| 5,964,778 | * | 10/1999 | Fugoso et al. .................. 606/194 |
| 6,010,521 | * | 1/2000 | Lee et al. ...................... 606/194 |

FOREIGN PATENT DOCUMENTS

| | | |
|---|---|---|
| 0 124 955 | 2/1984 | (EP) . |
| 0747 070 | 12/1996 | (EP) . |
| WO 92/08512 | 5/1992 | (WO) . |
| WO 93/15781 | 8/1993 | (WO) . |
| WO 94/00176 | 1/1994 | (WO) . |
| WO 95/09667 | 4/1995 | (WO) . |
| WO 96/03163 | 2/1996 | (WO) . |

\* cited by examiner

Primary Examiner—Sharon Kennedy
Assistant Examiner—Chris L. Rodriguez
(74) Attorney, Agent, or Firm—Heller Ehram White & McAuliffe

(57) ABSTRACT

An intraluminal catheter, particularly a dilatation catheter for angioplasty procedures, which has a shaft section formed of a blend of lubricous and bonding polymeric components in proportions to maintain a low coefficient of friction while maintaining the ability to bond non-lubricous polymeric material, such as polyethylene terephthalate, nylon, or PEBAX, to the segment.

20 Claims, 3 Drawing Sheets

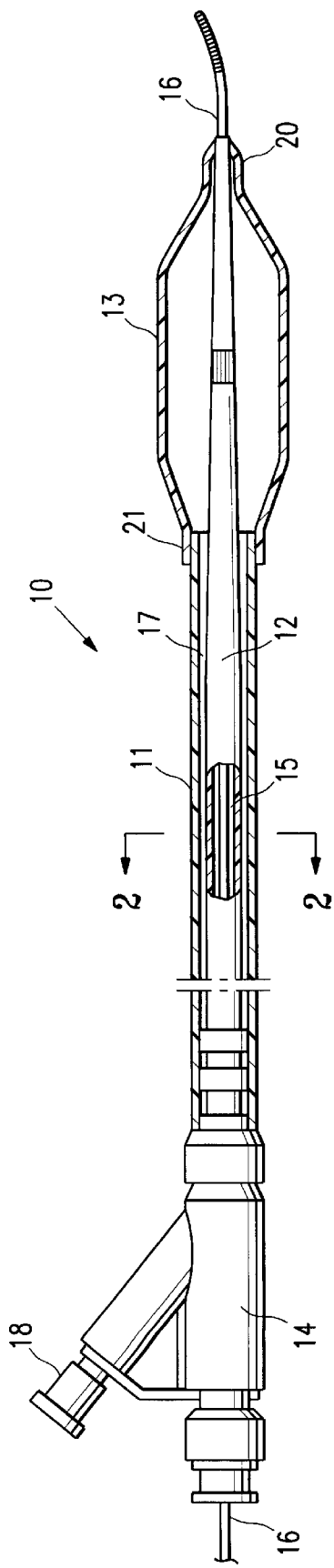
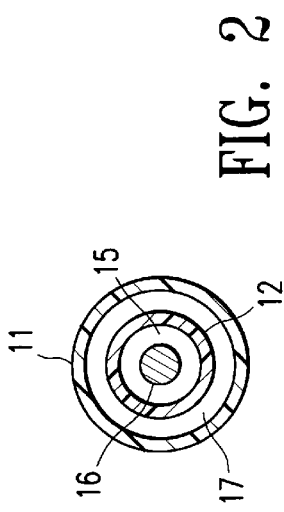
FIG. 1
FIG. 2

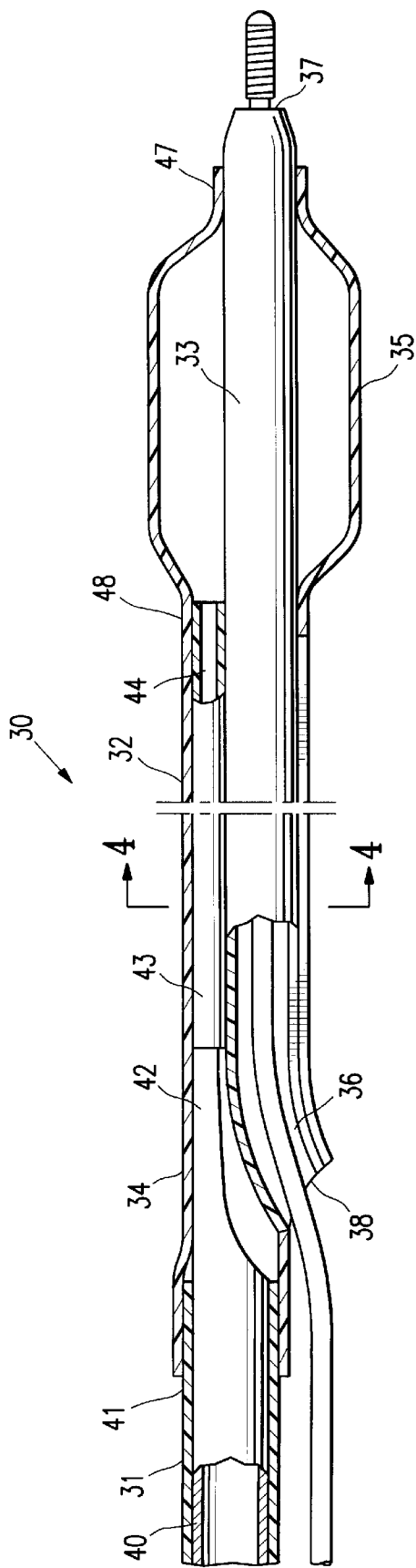
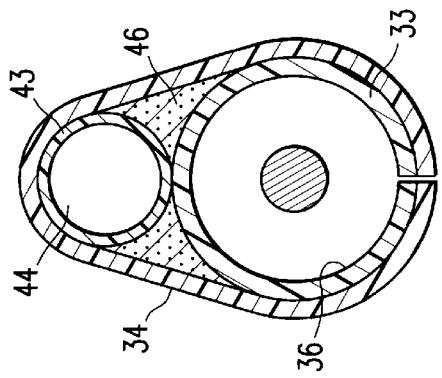
FIG. 3
FIG. 4

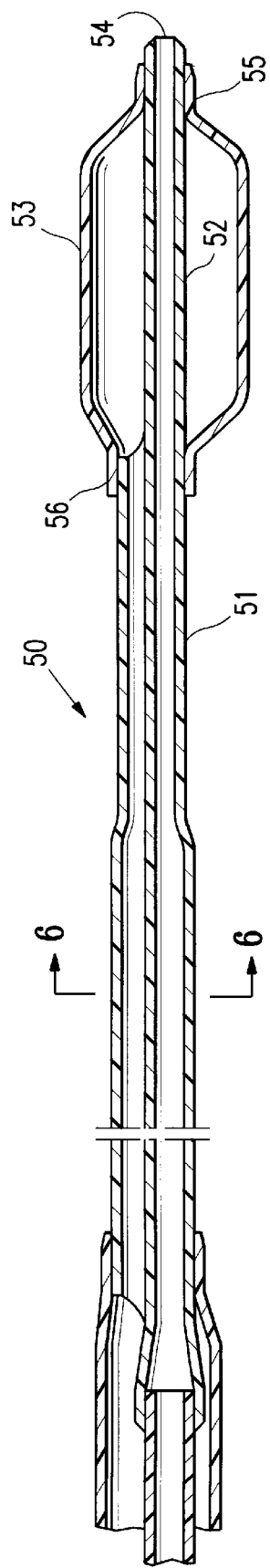
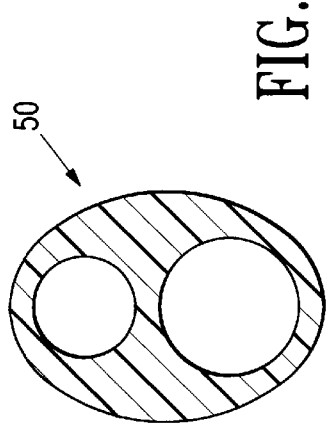
FIG. 5
FIG. 6

LUBRICOUS AND READILY BONDABLE CATHETER SHAFT

This application is a continuation-in-part application of copending application Ser. No. 08/976,447, filed Nov. 25, 1997, which is a continuation of application Ser. No. 08/587,330, filed Jan. 16, 1996, now abandoned.

BACKGROUND OF THE INVENTION

This invention relates to catheters for performing intravascular procedures such as percutaneous transluminal coronary angioplasty (PTCA) and more specifically to elongated shafts for such catheters.

PTCA is now one of the most widely used treatment modalities for heart disease. The procedure basically comprises advancing a dilatation catheter, having an inflatable balloon on its distal extremity, into the patient's coronary anatomy over a guidewire until the balloon of the dilatation catheter is properly positioned across the lesion to be dilated. Once properly positioned, the dilatation balloon is inflated with liquid to a predetermined size at relatively high pressures, e.g. up to 20 atmospheres or more, to expand the arterial passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed therefrom.

In most PTCA procedures, a guiding catheter having a preshaped distal tip is first percutaneously introduced into the cardiovascular system of a patient by means of a conventional Seldinger technique and advanced therein until the preshaped distal tip of the guiding catheter is disposed within the aorta adjacent to the ostium of the desired coronary artery. The guiding catheter is twisted or torqued from its proximal end, which extends out of the patient, to guide the distal tip of the guiding catheter into the desired coronary ostium. Once the guiding catheter is in proper position within the patient's vasculature, the dilatation catheter with a guidewire slidably disposed within an inner lumen of the dilatation catheter is positioned within the inner lumen of the guiding catheter. The guidewire is first advanced out the distal tip of the guiding catheter seated in the coronary ostium into the patient's coronary artery and directed to the region of the patient's coronary anatomy where the procedure is to occur. A torque may be applied to the proximal end of the guidewire, which extends out of the proximal end of the guiding catheter, to guide the curved or otherwise shaped distal end of the guidewire into a desired branch of the coronary artery. The advancement of the guidewire within the selected artery continues until it crosses the lesion to be dilated. The dilatation catheter is then advanced over the previously advanced guidewire, until the balloon on the distal extremity of the dilatation catheter is properly positioned across the lesion which is to be dilated.

Current intravascular catheter designs are limited by the need to incorporate conflicting characteristics. For example, most dilatation catheters are designed to be introduced into a body lumen over an in-place guidewire which is slidably received within an inner lumen within the catheter. As such, it is desirable to minimize the friction between the guidewire and the surface of the inner lumen of the catheter by constructing the catheter from a lubricous material such as a high density polyethylene. However, lubricous polymeric materials frequently lack other desirable properties, including, for example, the ability to readily bond to incompatible polymeric materials such as polyethylene terephthalate and nylon. Due to the high inflation pressures (up to 300 psi or more) associated with coronary balloon angioplasty, it is imperative to provide a strong bond between one or more ends of the dilatation balloon and the catheter shaft. Polyolefin balloons can be effectively fusion bonded to a polyethylene shaft but balloons made of nylon and other polyamide materials, and balloons made of polyesters such as polyethylene terephthalate do not easily bond to polyolefinic materials. Nylon and polyethylene terephthalate balloons usually require surface treatment and the use of a suitable adhesive to bond to polyolefin materials such as polyethylene. The additional manufacturing steps of surface treatments and incorporating and curing an adhesives, greatly complicate the manufacturing process and can introduce significant quality control problems. A catheter shaft should also have adequate strength for pushability and resistance to buckling or kinking. As another example, it may be desirable to provide a catheter shaft with elastomeric properties to improve flexibility. However, most lubricous materials are not elastomeric.

U.S. Pat. No. 5,304,134 to Kraus et al., which is hereby incorporated in its entirety by reference, attempts to provide a solution to the poor bonding of lubricous by providing the catheter shaft with an inner tubular member having a lubricous proximal portion and a non-lubricous, bondable distal portion. However, this approach does not represent a complete solution, because the lubricous proximal portion must still be bonded to the non-lubricous distal portion. The Kraus et al. system also requires that some portion of the guidewire lumen be formed from a non-lubricous material which restricts guidewire movement within the lumen.

A different approach involves forming the dilatation balloon as an integral portion of the catheter shaft itself, but this requires the balloon and the shaft to be formed from the same material, which is not always desirable because the property requirements for the balloon and the shaft can be quite different, particularly for dilatation catheters for PTCA.

Accordingly, there remains a need to provide a catheter shaft having a lubricous inner surface defining a guidewire lumen while allowing an easy, secure bond with a dilatation balloon or other catheter components formed of non-lubricous polymeric materials. The present invention satisfies these and other needs.

SUMMARY OF THE INVENTION

The present invention is directed to an intraluminal catheter, such as a balloon dilatation catheter for performing angioplasty procedures, which has a shaft or shaft segment which is both lubricous and is capable of readily bonding to other catheter components such as a balloon formed of essentially non-lubricous polymers.

In one embodiment of the invention, the catheter shaft or catheter shaft segment is formed of a polymeric blend comprising at least about 30% by weight, preferably at least about 50% by weight, of a lubricous polymeric component not more than about 60%, preferably not more than about 40%, of a bonding polymeric component and up to about 30%, preferably not more than about 10%, of a polymeric component for compatiblizing the lubricous and bonding components. Optionally, up to 25% by weight, usually not more than about 10% by weight of the blend could be a catalytic material to facilitate cross linking the shaft material to enhance compatiblizing. The lubricous component and the bonding component are not compatible, or miscible in the molten state. As used herein the term "compatible" and words of similar import mean that two polymer materials readily form an intimate mixture when they are melt processed together. However, the relative amounts of the different polymeric components of the polymeric blend will depends upon, and will therefore vary with, the nature of the polymeric materials.

Suitable lubricious polymeric components include polyolefins, such as polyethylene and polypropylene. One preferred lubricious polymeric material is high density polyethylene (HDPE), and most preferably high molecular weight HDPE having a molecular weight of about 50,000 to about 200,000. High density polyethylene has a density of at least about 0.94. The high molecular weight material has a high modulus of about 220,000 psi which provides improved collapse resistance for a given catheter shaft wall thickness.

In one embodiment, the bonding component comprises a polyamide polymeric material. Suitable polyamide materials include nylon, such as nylon 6, nylon 6,12, nylon 6,6, nylon 11, nylon 12. The preferred nylons are typically semicrystalline, although suitable amorphous nylons may also be used. In one embodiment, nylon 11 and nylon 12 are preferred due to their advantageously low moisture absorption, however, the lower nylons such as nylon 6 may also have low sensitivity to moisture when blended with the polyolefin lubricious polymeric component. Other suitable polyamide materials are copolyamides, including polyether block amides such as PEBAX available from Elf Atochem or PEBA available from Huls AG. Preferably the polyamides or copolyamides have a Shore D hardness of about 63 to about 75. Commercially available polyamide-polyolefin alloys or blends may be used, such as ORGALLOY resins, available from Elf Atochem. In the embodiment having a polyamide bonding component, the catheter shaft or shaft segment is preferably formed of a polymeric blend of at least about 20% by weight, preferably at least about 40% by weight, of a lubricious polymeric component; not more than about 80% by weight, preferably not more than about 60% by weight of a polyamide or copolyamide (bonding polymeric component); and about 5 to about 20% by weight of a compatiblizer. In one embodiment, the polymeric blend is about 20 to about 60% by weight of a lubricious polymeric component, about 40 to about 80% by weight of a polyamide or copolyamide bonding polymeric component, and about 5 to about 10% of a compatiblizer. Suitable compatiblizers for the polyamide containing blends include ethylene acrylic acid copolymer such as PRIMACOR from Dow Chemical, ethylene acrylate anhydride terpolymer such as LOTADER, or epoxy modified LOTADER, including AX8840, AX8900, AX9820 or AX8930 grades of LOTADER. An optional polymeric catalyst is preferably about 1 to about 10% by weight of the polymeric blend. Suitable. polymeric catalysts include ethylene acrylic ester-maleic anhydride terpolymer such as LOTADER XX1275, with 6% aliphatic tertiary amine. The catheter shaft having a polyamide polymeric bonding component, such as nylon or PEBAX, readily fusion bonds to a nylon or PEBAX polyamide balloon shaft.

In another embodiment, the bonding component comprises a copolyester such as HYTREL. The catheter shaft or shaft segment is formed of a polymeric blend comprising less than about 30% by weight, preferably less than about 50% by weight, of a lubricious polymeric component; and at least about 60%, preferably at least about 40%, of a copolyester (bonding polymeric material); and about 5 to about 20%, preferably about 5 to about 10%, compatiblizer. In one presently preferred embodiment, the catheter or catheter segment is formed of a blend of about 40–50% polyethylene (a lubricous component), about 50–60% of a copolyester such as Hytrel® (the bonding component), and up to about 5% of a compatiblizing agent such as ethylene acrylate anhydride terpolymer or epoxy modified ethylene acrylate anhydride terpolymer, or ethylene acrylic ester copolymer. A balloon formed of polyethylene terephthalate (PET) or copolyester such as HYTREL readily fusion bonds to the outer surface of the tubular member.

The polymer components are intimately mixed and extruded into a tubular product which is utilized as the inner tubular member of an intravascular catheter. The surface defining an inner lumen of the tubular member has a kinematic frictional coefficient of about 0.08 to about 0.3 on a smooth glass.

These and other advantages of the invention will become more apparent from the following detailed description of the invention when taken in conjunction with the accompanying exemplary drawings.

BRIEF DESCRIPTION OF THE DRAWINGS

FIG. 1 is an elevational view, partially in section, of an over-the-wire dilatation catheter having an inner tubular member embodying features of the invention.

FIG. 2 is a transverse cross section of the embodiment shown in FIG. 1 taken along the lines 2–2.

FIG. 3 is an elevational view, partially in section, of the distal section of a rapid exchange type dilatation catheter having an inner tubular member embodying features of the invention.

FIG. 4 is a transverse cross section of the embodiment shown in FIG. 3 taken along the lines 4–4.

FIG. 5 is an elevational view, partially in section, of an alternative embodiment wherein the distal section of the catheter shaft is formed of an extrusion of a polymer blend.

FIG. 6 is a transverse cross section of the embodiment shown in FIG. 5 taken along the lines 6–6.

DETAILED DESCRIPTION OF THE INVENTION

Reference is made to FIGS. 1 and 2 which illustrate a balloon dilatation catheter 10 embodying features of the invention. Generally, the catheter 10 comprises an outer tubular member 11, an inner tubular member 12, a dilatation balloon 13 on a distal portion of the catheter and an adapter 14 on the proximal end of the catheter. The inner tubular member 12 has a guidewire receiving inner lumen 15 which slidably receives guidewire 16. The outer surface of the inner tubular member 12 and the inner surface of the outer tubular member 11 define an annular inflation lumen 17 which is in fluid communication with the interior of balloon 13 and side arm 18 of adapter 14.

The distal skirt or shaft 20 of balloon 13 is bonded, preferably fusion bonded, to the exterior of the inner tubular member 12 and the proximal skirt 21 is fusion bonded to the exterior of the outer tubular member 11. The fusion bonds are preferably formed by applying laser energy to the exterior of the skirts 20 and 21 which causes the interface between the skirts and the exterior of the outer and inner tubular members 11 and 12. In one presently preferred embodiment, both the outer and inner tubular members 11 and 12 are formed of a polymer blend in accordance with the invention, having a lubricious polymeric component and a bonding polymeric component.

FIGS. 3–4 depict another embodiment of the invention directed to a rapid exchange type dilatation catheter 30. The catheter 30 includes a relatively stiff proximal shaft 31 formed of hypotubing and a relatively flexible distal shaft section 32. The distal shaft section 32 includes an inner tubular member 33, an outer tubular member 34 and a dilation balloon 35. The inner tubular member 33 has a guidewire receiving inner lumen 36 which is in fluid communication with a distal guidewire port 37 in the distal end of the catheter 30 and a proximal guidewire port 38 disposed a short distance, e.g. about 10 to about 45 cm from the proximal end of the balloon 35. The proximal shaft 31 comprises a metallic hypotube 40 (e.g. stainless steel or NiTi alloys) and an outer polymer jacket 41 formed of suitable polymer material such as high density polyethylene. The distal end 42 of the. hypotube 40 is truncated and fits into the interior of the outer tubular member 34 and bonded thereto by suitable adhesive. Support tube 43, preferably formed of polyimide, is disposed between the inner and outer tubular members 33 and 34 and defines inflation lumen 44. As shown in more detail in FIG. 4, the outer tubular member is partially bonded to the inner tubular member 33 and partially to the support tube 43. A filler material 46, such as 75/25 high density/low density polyethylene, is disposed between the outer tubular member 34 and the support tube 43.

In the embodiment of FIGS. 3–4 the inner tubular member 33 is formed of a polymer blend in accordance with the present invention. The distal skirt 47 of balloon 35 is fusion bonded to the exterior of the inner tubular member 33 as in the previously discussed embodiment shown in FIGS. 1 and 2. The proximal skirt 48 of the balloon 35 forms the outer tubular member 34 and is formed of essentially the same material as the balloon. In an alternative embodiment not shown the outer tubular member 34 may be a member separate and distinct from the balloon and formed of a polymer blend in accordance with the present invention. In this latter case the proximal skirt of the balloon 35 is fusion bonded to the exterior of the outer tubular member.

FIGS. 5 and 6 illustrate yet another embodiment of the invention wherein the catheter 50 has a distal shaft 51 which is of a dual lumen construction and is formed by extruding a polymer blend in accordance with the present invention. A tubular extension 52 extends through the interior of the dilatation balloon 53 and has a distal guidewire port 54 in its distal end. The balloon 53 has a distal skirt 55 fusion bonded to the distal end of the tubular extension 52 and a proximal skirt 56 fusion bonded to the distal shaft 51 as shown in the drawings.

One presently preferred polymer blend includes about 40 to about 60% high density polyethylene, about 40 to about 60% nylon, including nylon 12 or nylon 11, and about 5 to about 20% epoxy modified ethylene methyl acrylate such as LOTADER AX8900. Another preferred polymer blend comprises polyamidepolyolefin alloys, including alloys having nylon 6, and including ORGALLOY resins such as ORGALLOY RS, LE and LT grade resins, and preferably ORGALLOY LE 6000, 60XV, and LT 5050 extrudable grade resins. These blends readily fusion bond to balloons formed of polyamides such as nylon or PEBAX.

Another presently preferred polymer blend includes about 50% high density polyethylene, about 45% HYTREL (available from Dupont) and about 5% ethylene methyl acrylate such as epoxy modified LOTADER AX8900 (available from Elf ATOCHEM). This blend readily fusion bonds to a PET balloon and has a coefficient of friction of about 0.1–0.2. In one embodiment, the compatiblizing component is a polymeric material having a functional group selected from the group consisting of epoxy, anhydride, or acid functional groups. In another embodiment, the compatiblizing component is an alkyl acrylate copolymerized from monomers having about 2 to about 5 carbon atoms.

Although individual features of embodiments of the invention may be shown in some of the drawings and not in others, those skilled in the art will recognize that individual features of one embodiment of the invention can be combined with any or all the features of another embodiment. A variety of modifications can be made to the present invention without departing from the scope thereof.

What is claimed is:

1. An intraluminal catheter comprising an elongated shaft which has proximal and distal portions, and which has at least a segment fusion bonded to another catheter element, the segment being formed of a polymeric blend having a lubricous high density polymeric component and a bonding polyamide polymeric component.

2. The intraluminal catheter of claim 1 wherein the bonding polyamide polymeric component is selected from the group consisting of nylon and polyether block amide polymeric materials.

3. The intraluminal catheter of claim 1 wherein the bonding polyamide polymeric component is selected from the group consisting of nylon 6, nylon 11 and nylon 12.

4. The intraluminal catheter of claim 1 wherein the bonding polyamide polymeric component has a Shore hardness of about 63D to about 75D.

5. The intraluminal catheter of claim 1 wherein the bonding polyamide polymeric component comprises up to about 60% of the polymeric blend.

6. The intraluminal catheter of claim 1 wherein the high density polymeric component is polyethylene.

7. The intraluminal catheter of claim 1 wherein the high density polymeric component is polypropylene.

8. The intraluminal catheter of claim 1 wherein the lubricous high density polymeric component comprises at least 20% by weight of the polymeric blend.

9. The intraluminal catheter of claim 1 wherein the lubricous high density polymeric component comprises at least 40% by weight of the blend.

10. The intraluminal catheter of claim 1 wherein the catheter element is formed of non-lubricous polymeric material.

11. The intraluminal catheter of claim 1 wherein the catheter element is formed of a polymeric material selected from the group consisting of nylon and polyether block amide.

12. The intraluminal catheter of claim 1 wherein the catheter element is an inflatable member on the distal portion of the shaft.

13. The intraluminal catheter of claim 1 wherein the bonding component is compatiblized with the lubricous component by a compatiblizing component.

14. The intraluminal catheter of claim 13 wherein the compatiblizing component is a polymeric material having a functional group selected from the group consisting of epoxy, anhydride, or acid functional groups.

15. The intraluminal catheter of claim 13 wherein the compatiblizing component is an alkyl acrylate copolymerized from monomers having about 2 to about 5 carbon atoms.

16. The intraluminal catheter of claim 1 wherein the polymeric blend includes a catalytic polymeric component which catalyzes crosslinking of the bonding polymeric component and the polymeric compatiblizer.

17. A balloon catheter comprising:
a) an elongated shaft which has proximal and distal portions, and which has at least a segment formed of a polymeric blend having a lubricous high density polyolefin polymeric component and a bonding polyamide polymeric component; and
b) a balloon formed of non-lubricous material, having at least a portion fusion bonded to the shaft segment.

18. The catheter of claim 17 wherein the balloon is formed of a polymeric material selected from the group consisting of nylon and polyether block amide.

19. The intraluminal catheter of claim 1 wherein the lubricous high density polymeric component is a lubricous high density polyolefin polymeric component.

20. The intraluminal catheter of claim 1 wherein the segment comprises a polyamide-polyolefin alloy having a nylon 6 polyamide polymeric component.

* * * * *